United States Patent [19]

Sirdesai et al.

[11] Patent Number: 5,785,958
[45] Date of Patent: Jul. 28, 1998

[54] NON-YELLOWING RAPID DRYING NAIL POLISH TOP-COAT COMPOSITIONS

[75] Inventors: Sunil J. Sirdesai, Irvine; George Schaeffer, Beverly Hills, both of Calif.

[73] Assignee: OPI Products, Inc., North Hollywood, Calif.

[21] Appl. No.: 558,638

[22] Filed: Nov. 13, 1995

[51] Int. Cl.$^6$ .................. A61K 7/00; A61K 7/04
[52] U.S. Cl. ............................. 424/61; 424/401
[58] Field of Search ................. 424/61, 40; 132/73

[56] References Cited

U.S. PATENT DOCUMENTS

| | | | |
|---|---|---|---|
| 3,928,113 | 12/1975 | Rosenberg | 156/344 |
| 4,104,333 | 8/1978 | Lee, Jr. et al. | 260/885 |
| 4,126,675 | 11/1978 | Boulogne et al. | 424/61 |
| 4,596,260 | 6/1986 | Giuliano | 132/73 |
| 4,708,866 | 11/1987 | Turco et al. | 424/61 |
| 4,749,564 | 6/1988 | Faryniarz et al. | 424/61 |
| 5,118,495 | 6/1992 | Nafziger et al. | 424/61 |
| 5,130,125 | 7/1992 | Martin et al. | 424/61 |
| 5,407,666 | 4/1995 | Patel et al. | 424/61 |
| 5,456,905 | 10/1995 | Valenty | 424/61 |
| 5,512,273 | 4/1996 | Martin | 424/61 |
| 5,516,509 | 5/1996 | Marr-Leisy et al. | 424/61 |

*Primary Examiner*—Thurman K. Page
*Assistant Examiner*—Sharon Howard
*Attorney, Agent, or Firm*—Blakely Sokoloff Taylor & Zafman

[57] ABSTRACT

Rapid drying top coat used to provide a durable glossy look to manicured nails. The rapid-drying, durable coating composition is comprised of a base resin of cellulose acetate butyrate and an aliphatic ester monomer. Additional components include a film former, a cross-linking agent, an inhibitor to polymerization and a solvent. The rapid drying nail polish top-coat composition cures to a hard durable finish within a few minutes on exposure either to safe dosage of ultraviolet light or any heat source depending whether the formulation contains a photoinitiator or thermal initiator. This process of curing also aids in drying the inner layers of nail polish application by evaporating the solvents in these layers. The top coats are non-toxic and exhibit an unique property of non-yellowing.

30 Claims, No Drawings

NON-YELLOWING RAPID DRYING NAIL POLISH TOP-COAT COMPOSITIONS

1. Field of the Invention

This invention relates to human finger and toe nail polish and more particularly to the top coats used by individuals and professional manicurists and pedicurists within the cosmetic industry to provide smooth, hard, and glossy coatings over nail polish.

2. Background of the Invention

The following protocol is normally used for better adhering of nail polish to human nails and to provide a glossy and durable finish. First, a base coat is applied, followed by two coats of nail polish. A top coat is then applied to provide a glossy look and to protect manicured nails. Thus, the ordinary application of glossy, durable nail polish is actually a four coat process. This process, including drying time, takes a very long time, amounting to considerable inconvenience to the individuals that wear nail polish.

Various methods have been devised to alleviate the burden on individuals applying nail polish or having nail polish applied to their nails. One method involves the application of an external light or heat source to expedite the drying time. Fingerlin (1941) in U.S. Pat. No. 2,262,274 and Corbett (1945) in U.S. Pat. No. 2,374,472 invented devices to expedite the drying process in the application of nail polish. Essentially, these devices are box-like dryers that blow hot or cold air for a specified time. This helps in the evaporation of volatile solvents from the surface (i.e., the top coat), thereby giving a false impression of dryness since the layers underneath the top coat are not dry.

Commercially available, clinically safe infrared lamps have also been used to reduce the drying time by photocurable means. Infrared lamps can evaporate solvents in the inner layers of the nail polish and reduce the typical application process to about a 30 minute process. Nevertheless, 30 minutes is still a long wait for drying the topcoat in this fast-paced world.

Various formulations have also been developed to expedite the process of the application of nail polish. Rosenberg (1975) in his U.S. Pat. No. 3,928,113 describes a photocurable nail lacquer designed specifically for a water soluble or water swellable base coat comprising one or more vinylic compounds. The water soluble base coat is very impractical since there is no way of avoiding the wetting of nails with water in the normal course of the day. Wetting the nails with water would dissolve or swell the base coat and the entire nail polish application could be damaged.

Giulano (1986) in his U.S. Pat. No. 4,596,260 describes the use of solvent-free, photocurable liquid compositions to be used with an adhered, artificial nail tip. After the artificial nail tip has been adhered to the natural nail tip, a continuous coating is applied over the artificial nail tip and at least a portion of a natural nail to give the appearance of a natural nail. This photocurable liquid upon exposure to ultraviolet light yields a densely crosslinked plastic. Commercial nail polish removers cannot remove this plastic coating from the nail, making this coating composition very impractical for ordinary use.

Nafziger (1992) in his U.S. Pat. No. 5,118,495 describes a photocurable top coat using nitrocellulose as the base resin, a photo-reactive monomer, a photoinitiator and an inhibitor to polymerization. Though this formulation addresses most of the problems encountered in the earlier inventions (i.e., drying time, durability), its biggest limitation is that the formulation contains nitrocellulose. Nitrocellulose is responsible for the rapid yellowing of the top coat over a very short period of time. This drawback in the formulation results in the discoloration of the original nail polish shade, especially in light shades, to an unsightly yellowish color. "Yellowing" of the nail polish shade is a serious drawback in the color conscious beauty industry.

Martin (1992) in his U.S. Pat. No. 5,130,125 describes a quick drying coat with core formulations consisting of cellulose acetate butyrate dissolved in toluene and n-butyl acetate with a plasticizer butyl benzyl benzoate in isopropyl alcohol and siloxanes. This formulation gives an illusion that the top coat is dry by providing a non-tacky slippery surface. Martin fails to address the problem of the drying of the solvents in the inner layers of the application. Moreover, these formulations incorporate toluene, an established toxin, into the core formulation as an essential component.

The general art also reveals a quick drying top coat using nitrocellulose, cellulose acetate butyrate, acrylic resin in a solvent mixture of esters, alcohol and ketone. This top coat dries quickly on exposure to any source of heat due to evaporation of low boiling solvents and not by way of any curing process. As noted earlier, the presence of nitrocellulose in the formulation is responsible for the unsightly yellowing of this general art top coat which is a major drawback in its application.

There exists a need for a top-coat composition that expedites the drying time of the nail polish application process but is also non-toxic and will not cause unsightly "yellowing" or discoloration of the polish.

SUMMARY AND OBJECTS OF THE INVENTION

This invention relates to an improved rapid drying top-coat composition for application with nail polish and a method for applying glossy, durable nail polish utilizing the top-coat composition. The invention relates to a top-coat composition that dries within three minutes under exposure to safe dosages of low intensity light or any heat source. The compositions are particularly useful for application over light nail polish shades by virtue of their non-yellowing properties thereby eliminating the discoloration problem prevalent with existing top coats. Besides providing a glossy and durable finish, the curing of the top-coat composition also aids in the evaporation of the solvents in the inner layers of the application process (i.e., base coat, nail polish coats). The compositions are also non-toxic and can be removed with any commercial nail polish remover.

The top coat coating composition dries in approximately three minutes upon exposure to safe amounts of ultraviolet light (photoreactive) or heat (thermal reactive). The photoreactive coating composition of the invention is comprised of: A base resin of cellulose acetate butyrate, from 5 to 50 percent by weight of the total composition; a film former of methacrylate polymer from 5 to 20 percent by weight of the total composition; an acetate or alcohol solvent at least 1.5 times the amount by weight of the base resin; a monomer of an aliphatic ester of methacrylic acid from 0.5 to 20 percent by weight of the total composition; a cross-linking agent from 0.1 to 5 percent by weight of the total composition; a photoinitiator from 0.05 to 3 percent by weight of the total composition; and an inhibitor to polymerization from 5–15 parts per million of the total composition.

The thermal reactive coating composition of the invention is similar to the photoreactive coating composition except that a thermal initiator is substituted for the photoinitiator of the photoreactive coating composition.

The top coat is applied in the final step of the nail polish application process. The first coat in the application process is a base coat which is applied to fill the ridges in the nail. This is followed by two coats of nail polish to provide a rich look. The top coat is finally applied to provide a glossy and durable finish to the manicured nail. The invention relates to the top coat. The drying process of the top coat of the invention involves curing of the monomers present in the composition to form hard, durable and glossy polymers on exposure either to ultraviolet light or thermal radiation depending on the choice of initiator in the composition. The curing process takes about three minutes and yields a top coat that is resistant to denting or smearing upon accidental brushing of the manicured nails. In about ten minutes, the curing process is complete, thereby providing the top coat with a tough and glossy finish.

The curing process also aids in the drying of the underlying nail polish. This is because curing is essentially a polymerization process. Polymerization of monomers is an exothermic reaction and this generates heat. The generated heat aids in the volatilization of the solvents in the nail polish.

The top coat of the invention possesses excellent gloss and extended wear similar to other commercially available top coats. However, unlike the commercially available top coats that have yellowing or discoloration problems or contain a toxic component in their compositions, the invention provides a non-yellowing, non-toxic, hard, durable and glossy top-coat composition.

The application of the top coat of the invention requires no special procedures. Overlaying the top-coat composition of the invention over nail polish can be carried out by standard coating procedures (i.e., brushing) already known to those of ordinary skill in the art. Further, as noted above, Applicants have discovered that by switching the initiators in the formulation, one can have either a heat curable or a photocurable top-coat composition depending on the drying means available.

In today's color conscious cosmetic industry, the unique non-yellowing property of the rapid dry top-coat compositions of the invention make it ideal for application over nail polish, particularly light shades, as it does not discolor the original nail polish shades. These top-coat compositions are non-toxic and can be removed without difficulty using commercial nail polish removers.

DETAILED DESCRIPTION OF THE INVENTION

The invention relates to a coating composition for application over nail polish and a method for applying glossy, durable nail polish that utilizes the coating composition. The coating composition dries rapidly upon exposure to safe amounts of ultraviolet light or thermal radiation to yield a clear, glossy, hard, and durable finish that will not fade to a yellow tint over time. The coating composition is non-toxic and is removable with common, commercially available polish remover.

The invention is comprised of a base resin which is cellulose acetate butyrate, a film former which is a methacrylate polymer, thermally curable or photocurable monomers which are monofunctional methacrylates and cross-linkers (i.e., difunctional and trifunctional methacrylates), a thermal initiator or photoinitiator(s) together in a solution of aliphatic esters and alcohol.

Cellulose acetate butyrate is used as the base resin for its ability to not produce a yellow tint over time. Most top-coat compositions use nitrocellulose as a base resin and nitrocelluolose dries to an unsightly yellow tint over time. Cellulose acetate butyrate does not yield an unsightly "yellowing" of the nail polish over time. Commercially available cellulose acetate butyrate contemplated for use in the invention include Cellulose Acetate Butyrate 381-0.5 and Cellulose Acetate Butyrate 381-2.0, both distributed by Eastman Chemicals. The invention contemplates, for example, that either Cellulose Acetate Butyrate 381-0.5 or Cellulose Acetate Butyrate 381-2.0, or a combination of both may be used as the base resin of the coating composition. Cellulose acetate butyrate 381-0.5 is used in concentrations between 20% and 50% by weight of the total composition. The preferred concentrations for cellulose acetate butyrate 381-0.5 is in the range of 30% by weight of the total composition. Cellulose acetate butyrate 381-2.0 is used in concentrations between 5% and 20% by weight of the total composition. The preferred concentrations for cellulose acetate butyrate 381-2.0 is in the range of 10% of the total composition.

Methacrylate polymers are used as a film former in the coating composition of the invention. The methacrylate polymer is used in concentrations between 5% and 20% by weight of the total composition. The preferred concentrations is in the range of 11% of the total composition. Commercially available methacrylate polymers suitable for use in the coating composition of the invention include methyl methacrylate/butyl methacrylate copolymer, "Rohagum PM 685" (distributed by Rohm Tech) and methyl methacrylate/butyl methacrylate/methacrylic acid terpolymer, "Dianal BR-106" (distributed by Dianal America, Inc.), although the invention does not contemplate being limited to these commercially available methacrylate polymers.

The coating composition utilizes a solvent or a mixture of solvents in an amount equivalent to 1.5 times the amount by weight of the base resin. Suitable solvents include acetates and alcohols, particularly ethyl acetate, butyl acetate, and isopropyl alcohol. The preferred embodiment utilizes a mixture of solvents in varying ratios to obtain the desired viscosity. The invention contemplates that any non-toxic or safe solvent may be used.

The photoreactive coating composition of the invention includes photoreactive monomers. Preferred photoreactive monomers include the following methacrylate monomers: Cyclohexyl methacrylate, n-decyl methacrylate, 2-ethyl hexyl methacrylate, ethyl methacrylate, hydroxy propyl methacrylate, isobornyl methacrylate, 2-methoxy ethyl methacrylate. Aromatic esters of methacrylic acid are avoided in the invention due to their tendency to produce a yellowish color. Acrylate monomers were not considered due to their tendency to cause dermatitis. Neither cellulose acetate butyrate nor methacrylate copolymer act as chain transfer agents in the polymerization process, thereby allowing the methacrylate monomers to cure to a hard, durable finish upon thermal initiation or photoinitiation. The methacrylate monomers are used in the ranges 0.5%–20% of the total composition.

The photoreactive coating composition of the invention also includes difunctional and trifunctional methacrylate monomers, cross-linking agents, in the ranges 0.1%–5% of the total composition. Commercially available cross-linking agents suitable for use in the invention include diurethane dimethacrylate, ethylene glycol dimethacrylate, 1,10 decanediol dimethacrylate, 1,6-hexanediol dimethacrylate, and trimethylolpropane trimethacrylate.

The photoreactive coating composition includes photoinitiators in the ranges between 0.05 and 3% by weight of the total composition. Commercially available photoinitiators suitable for use in the invention include benzoin methyl ether, 2-hydroxy-2-methyl-1-phenyl-1-propanone ("Darocur 1173"), diethoxyacetophenone, and benzyl diketal. A photoinitiator can either be used alone in the invention or in combination with a cophotoinitiator. The cophotoinitiators suitable for use with a photoinitiator in the invention are oligomeric mixtures of phenyl propanones. Oligomeric mixtures of phenyl propanones such as a mixture of 2,4,6-trimethylbenzophenone and 4-methylbenzophenone and a mixture of oligo-[2-hydroxy-2-methyl-1[4-(1-methylvinyl)phenyl]propanone] and 2-hydroxy-2-methyl-phenyl propanone that are sold by Sartomer under the names "Esacure KIP 100F" and "Esacure TZT Photoinitiator".

Finally, the photoreactive coating composition includes inhibitors to polymerization in an amount of between 5 and 15 ppm of the total composition. Typical inhibitors suitable for use in the invention include hydroquinone and 4-methoxy phenol.

The thermal reactive coating composition of the invention is similar to the photoreactive coating composition except that a thermal initiator is used instead of a photoinitiator or a photoinitiator/cophotoinitiator. Examples of thermal initiators that are suitable for the invention include benzoyl peroxide and coumarin peroxide. Thermally-curable coating compositions have been developed wherein the heat source is a 55 watt bulb. As noted above, thermally-curable coating composition possess the same properties as the photocurable coating compositions: rapid-drying, durable, non-yellowing.

The following examples of top-coat compositions are given below.

EXAMPLE 1

| Ingredient | Weight Percent |
| --- | --- |
| Ethyl Acetate | 40 |
| Butyl Acetate | 30 |
| Isopropyl Alcohol | 4.2 |
| Ethyl Methacrylate | 3.0 |
| Ethylene Glycol Dimethacrylate | 0.3 |
| Darocur 1173 | 0.3 |
| Rohagum PM 685 | 11 |
| Cellulose Acetate Butyrate 381-0.5 | 6.7 |
| Cellulose Acetate Butyrate 381-2.0 | 4.5 |
| 4-Methoxy Phenol | 5 ppm |

EXAMPLE 2

| Ingredient | Weight Percent |
| --- | --- |
| Ethyl Acetate | 40 |
| Butyl Acetate | 30 |
| Isopropyl Alcohol | 4.2 |
| Ethyl Methacrylate | 3.0 |
| Ethylene Glycol Dimethacrylate | 0.3 |
| Benzoyl Peroxide | 0.3 |
| Dianal BR-106 | 11 |
| Cellulose Acetate Butyrate 381-0.5 | 6.7 |
| Cellulose Acetate Butyrate 381-2.0 | 4.5 |
| 4-Methoxy Phenol | 5 ppm |

EXAMPLE 3

| Ingredient | Weight Percent |
| --- | --- |
| Ethyl Acetate | 40 |
| Butyl Acetate | 30 |
| Isopropyl Alcohol | 4.2 |
| Ethyl Methacrylate | 3.0 |
| Ethylene Glycol Dimethacrylate | 0.3 |
| Darocur 1173 | 0.3 |
| Rohagum PM 685 | 5.5 |
| Dianal BR-106 | 5.5 |
| Cellulose Acetate Butyrate 381-0.5 | 6.7 |
| Cellulose Acetate Butyrate 381-2.0 | 4.5 |
| 4-Methoxy Phenol | 5 ppm |

EXAMPLE 4

| Ingredient | Weight Percent |
| --- | --- |
| Ethyl Acetate | 40 |
| Butyl Acetate | 30 |
| Isopropyl Alcohol | 4.2 |
| Ethyl Methacrylate | 3.0 |
| 1,6 Hexanediol Dimethacrylate | 0.3 |
| Benzoyl Peroxide | 0.3 |
| Rohagum PM 685 | 11 |
| Cellulose Acetate Butyrate 381-0.5 | 5.6 |
| Cellulose Acetate Butyrate 381-2.0 | 5.6 |
| Hydroquinone | 5 ppm |

EXAMPLE 5

| Ingredient | Weight Percent |
| --- | --- |
| Ethyl Acetate | 40 |
| Butyl Acetate | 30 |
| Isopropyl Alcohol | 4.2 |
| Ethyl Methacrylate | 2.0 |
| 2-Methoxy Ethyl Methacrylate | 1.0 |
| 1,6 Hexanediol Dimethacrylate | 0.3 |
| Coumarin Peroxide | 0.3 |
| Rohagum PM 685 | 11 |
| Cellulose Acetate Butyrate 381-0.5 | 11.2 |
| Hydroquinone | 5 ppm |

EXAMPLE 6

| Ingredient | Weight Percent |
| --- | --- |
| Ethyl Acetate | 31 |
| Butyl Acetate | 30 |
| Isopropyl Alcohol | 4.2 |
| Ethyl Methacrylate | 10.4 |
| 2-Ethyl Hexyl Methacrylate | 9 |
| Diurethane Dimethacrylate | 0.3 |
| Diethoxy Acetophenone | 0.4 |
| Esacure TZT Photoinitiator | 0.2 |
| Rohagum PM 685 | 9 |
| Cellulose Acetate Butyrate 381-0.5 | 5.5 |
| 4-Methoxy Phenol | 10 ppm |

EXAMPLE 7

| Ingredient | Weight Percent |
| --- | --- |
| Ethyl Acetate | 31 |
| Butyl Acetate | 30 |
| Isopropyl Alcohol | 3.2 |
| n-Decyl Methacrylate | 9 |
| Isobornyl Methacrylate | 8.2 |
| 1,10 Hexanediol Dimethacrylate | 1.2 |
| Benzyl Diketal | 0.7 |
| Esacure KIP 100F | 0.2 |
| Rohagum PM 685 | 11 |
| Cellulose Acetate Butyrate 381-0.5 | 5.5 |
| 4-Methoxy Phenol | 15 ppm |

EXAMPLE 8

| Ingredient | Weight Percent |
| --- | --- |
| Ethyl Acetate | 31 |
| Butyl Acetate | 32 |
| Isopropyl Alcohol | 4.2 |
| Cyclohexyl Methacrylate | 10 |
| Hydroxy Propyl Methacrylate | 9.4 |
| Diurethane Dimethacrylate | 0.3 |
| Benzoin Methyl Ether | 0.4 |
| Esacure TZT Photoinitiator | 0.2 |
| Rohagum PM 685 | 11 |
| Cellulose Acetate Butyrate 381-0.5 | 5.5 |
| 4-Methoxy Phenol | 10 ppm |

EXAMPLE 9

The following presents a formulation procedure for making a thermal reactive top-coat composition of the instant invention.

(1) Mix Ethyl Acetate, Butyl Acetate, Isopropyl Alcohol, Ethyl Methacrylate with inhibitor, Ethylene Glycol Dimethacrylate with inhibitor, and Benzoyl Peroxide. Start stirring this mixture.

(2) In the meantime weigh Rohagum PM 685. Slowly add Rohagum to this mixture. Stir for 30 minutes. (Rohagum should be completely dissolved by now.)

(3) Add Cellulose Acetate Butyrate 381-0.5 to the mixture above and stir for 45 minutes. (CAB 381-0.5 should be dissolved by now.)

(4) Add Cellulose Acetate Butyrate 381-2.0 slowly to the above mixture. Stir for 45 minutes. (CAB 381-2.0 should be dissolved by now.)

(5) Stir gently for half hour. (No disperser)

The composition is now ready to be filled in bottles.

EXAMPLE 10

The following presents a formulation procedure for making a photoreactive top-coat composition of the instant invention:

(1) Mix Ethyl Acetate, Butyl Acetate, Isopropyl Alcohol, Ethyl Methacrylate with inhibitor, Ethylene Glycol Dimethacrylate with inhibitor, and Darocur 1173. Start stirring this mixture.

(2) In the meantime weigh Rohagum PM 685. Slowly add Rohagum to this mixture. Stir for 30 minutes. (Rohagum should be completely dissolved by now.)

(3) Add Cellulose Acetate Butyrate 381-0.5 to the mixture above and stir for 45 minutes. (CAB 381-0.5 should be dissolved by now.)

(4) Add Cellulose Acetate Butyrate 381-2.0 slowly to the above mixture. Stir for 45 minutes. (CAB 381-2.0 should be dissolved by now.)

(5) Stir gently for half hour. (No disperser)

The composition is now ready to be filled in bottles.

In the preceding detailed description, the invention is described with reference to specific exemplary embodiments thereof. Further, the description made reference to commercially available components for use in embodiments of the invention. It will, however, be evident to those of ordinary skill in the art that various modifications and changes may be made thereto without departing from the broader spirit and scope of the invention as set forth in the claims. The specification is to be regarded in an illustrative rather than a restrictive sense.

What is claimed is:

1. A coating composition for application over nail polish, consisting of:

a base resin of cellulose acetate butyrate, from 5 to 50% by weight of the total composition;

a monomer of an aliphatic ester of methacrylic acid from 0.5 to 20% by weight of the total composition;

a film former of methacrylate polymer from 5 to 20% by weight of the total composition;

a cross-linking agent; and an initiator of polymerization, wherein the composition forms a durable coating with a substantially clear appearance.

2. The coating composition of claim 1, further consisting of a solvent at least 1.5 times by weight of the base resin.

3. The coating composition of claim 1, wherein said cross-linking agent is selected from the group consisting of diurethane dimethacrylate, ethylene glycol dimethacrylate, and 1,10 decanediol dimethacrylate from 0.1 to 5% by weight of the total composition.

4. The coating composition of claim 1, wherein said initiator is a photoinitiator selected from the group consisting of benzoin methylether, 2-hydroxy-2-methyl-1-phenyl-1-propanone ("Darocur 1173") diethoxyacetophenone, and benzyldiketal from 0.05 to 3% by weight of the total composition.

5. The coating composition of claim 1, further consisting of an inhibitor to polymerization selected from the group consisting of hydroquinone and 4-methoxy phenol from 5–15 ppm of the total composition.

6. The coating composition of claim 1, wherein said initiator is a thermal initiator selected from the group consisting of benzoyl peroxide and coumarin peroxide from 0.05 to 3% by weight of the total composition.

7. The coating composition of claim 1, further consisting of an inhibitor to polymerization selected from the group consisting of hydroquinone and 4-methoxy phenol from 5–15 ppm of the total composition.

8. A photoreactive coating composition for application over nail polish, consisting of:

a base resin of cellulose acetate butyrate, from 5 to 50 percent by weight of the total composition;

a film former of methacrylate polymer from 5 to 20 percent by weight of the total composition;

a solvent at least 1.5 times the amount by weight of the base resin;

a monomer of an aliphatic ester of methacrylic acid from 0.5 to 20 percent by weight of the total composition;

a cross-linking agent selected from the group consisting of diurethane dimethacrylate, ethylene glycol dimethacrylate, and 1,10 decanediol dimethacrylate from 0.1 to 5 percent by weight of the total composition;

a photoinitiator selected from the group consisting of benzoin methyl ether, 2-hydroxy-2-methyl-1-phenyl-1-propanone, diethoxyacetophenone, and benzyl diketal from 0.05 to 3 percent by weight of the total composition; and an inhibitor to polymerization selected from the group consisting of hydroquinone and 4-methoxy phenol from 5–15 ppm of the total composition, wherein the composition forms a durable coating with a substantially clear appearance.

9. A photoreactive coating composition for application over nail polish, comprising:

a base resin of cellulose acetate butyrate, from 5 to 50 percent by weight of the total composition and free of a chemically significant amount of nitrocellulose;

a film former of methacrylate polymer from 5 to 20 percent by weight of the total composition;

a solvent at least 1.5 times the amount by weight of the base resin;

a monomer of an aliphatic ester of methacrylic acid from 0.5 to 20 percent by weight of the total composition;

a cross-linking agent selected from the group consisting of diurethane dimethacrylate, ethylene glycol dimethacrylate, and 1,10 decanediol dimethacrylate from 0.1 to 5 percent by weight of the total composition;

a photoinitiator selected from the group consisting of benzoin methyl ether, 2-hydroxy-2-methyl-1-phenyl-1-propanone, diethoxyacetophenone, and benzyl diketal from 0.05 to 3 percent by weight of the total composition and a cophotoinitiator selected from the group consisting of a mixture of oligo[2-hydroxy-2-methyl-1-[4-(1-methylvinyl phenyl]propanone and 2-hydroxy-2-methyl-phenyl propanone and a mixture of 2,4,6-trimethylbenzophenone and 4-methylbenzophenone, an inhibitor to polymerization selected from the group consisting of hydroquinone and 4-methoxy phenol from 5–15 ppm of the total composition.

10. The composition of claim 8, wherein the film former is a methacrylate copolymer or a methacrylate terpolymer.

11. The composition of claim 10, wherein the film former is selected from the group consisting of methyl methacrylate/butyl methacrylate copolymer and methyl methacrylate/butyl methacrylate/methacrylic acid terpolymer.

12. The composition of claim 11, wherein the film former is selected from the group consisting of a copolymer of methyl methacrylate/butyl methacrylate and a terpolymer of methyl methacrylate/butylmethacrylate/methacrylic acid.

13. The composition of claim 8, wherein the solvent is selected from the group consisting of ethyl acetate, butyl acetate, and isopropyl alcohol.

14. The composition of claim 8, wherein the base resin is a mixture of cellulose acetate butyrate 381-0.5 and cellulose acetate butyrate 381-2.0.

15. A thermal reactive coating composition for application over nail polish, consisting of:

a base resin of cellulose acetate butyrate, from 5 to 50 percent by weight of the total composition;

a film former of methacrylate polymer from 5 to 20 percent by weight of the total composition;

an acetate or alcohol solvent at least 1.5 times the amount by weight of the base resin;

a monomer of an aliphatic ester of methacrylic acid from 0.5 to 20 percent by weight of the total composition;

a cross-linking agent selected from the group consisting of diurethane dimethacrylate, ethylene glycol dimethacrylate, and 1,10 decanediol dimethacrylate from 0.1 to 5 percent by weight of the total composition;

a thermal initiator selected from the group consisting of benzoyl peroxide and coumarin peroxide from 0.05 to 3 percent by weight of the total composition; and an inhibitor to polymerization selected from the group consisting of hydroquinone and 4-methoxy phenol, wherein the composition forms a durable coating with a clear appearance.

16. The composition of claim 15, wherein the film former is a methacrylate copolymer or a methacrylate terpolymer.

17. The composition of claim 16, wherein the film former is selected from the group consisting of methyl methacrylate/butyl methacrylate copolymer and methyl methacrylate/butyl methacrylate/methacrylic acid terpolymer.

18. The composition of claim 17, wherein the methacrylate polymer is selected from the group consisting of a copolymer of methyl methacrylate/butyl methacrylate and a terpolymer of methyl methacrylate/butylmethacrylate/methacrylic acid.

19. The composition of claim 15, wherein the solvent is selected from the group consisting of ethyl acetate, butyl acetate, and isopropyl alcohol.

20. The composition of claim 15, wherein the base resin is a mixture of cellulose acetate butyrate 381-0.5 and cellulose acetate butyrate 381-2.0.

21. A method for applying nail polish to a human nail, the method comprising:

applying a nail polish composition;

applying a top coat photoreactive composition for application over nail polish, consisting of:

a base resin of cellulose acetate butyrate from 5 to 50 percent by weight of the total composition;

a film former of methacrylate polymer from 5 to 20 percent by weight of the total composition;

a monomer of an aliphatic ester of methacrylic acid from 0.5 to 20 percent by weight of the total composition;

a cross-linking agent selected from the group consisting of diurethane dimethacrylate, ethylene glycol dimethacrylate, and 1,10 decanediol dimethacrylate from 0.1 to 5 percent by weight of the total composition; and an inhibitor to polymerization selected from the group consisting of hydroquinone and 4-methoxy phenol from 5–15 ppm of the total composition.

22. The method of claim 21, wherein the nail is exposed to a drying source.

23. The method of claim 22, wherein the drying source is an ultraviolet light source, and wherein the top-coat composition further consists of a photoinitiator selected from the group consisting of benzoin methyl ether, 2-hydroxy-2-methyl-1-phenyl-1-propanone, diethoxyacetophenone, and benzyl diketal from 0.05 to 3 percent by weight of the total composition.

24. A method for applying nail polish to a human nail, the method comprising:

applying a nail polish composition;

applying a topcoat composition for application over said nail polish composition comprising:

a base resin of cellulose acetate butyrate, and free of a chemically significant amount of nitrocellulose, from 5 to 50 percent by weight of the total composition;

a film former of methacrylate polymer from 5 to 20% by weight of the total composition;

a monomer of an aliphatic ester of methacrylic acid from 0.5 to 20 percent by weight of the total composition;

a cross-linking agent selected from the group consisting of diurethane dimethacrylate, ethylene-glycol dimethacrylate and 1,10 decanediol dimethacrylate from 0.1 to 5 percent by weight of the total composition;

an inhibitor to polymerization selected from the group consisting of hydroquinone and 4-methoxy phenol from 5 to 15 parts per million of the total composition; and a photoinitiator selected from the group consisting of benzoin methyl ether, 2-hydroxy-2-methyl-1-phenyl-1-propenone, diethoxyacetophenone, and benzyl diketal from 0.5 to 3 percent by weight of the total composition, and a cophotoinitiator selected from the group consisting of a mixture of oligo[2-hydroxy-2-methyl-1-[4-1-methylvinyl phenyl]propanone and 2-hydroxy-2-methyl-phenyl propanone and a mixture of 2,4,6-trimethylbenzophenone and 4-methylbenzophenone.

25. The method of claim 22, wherein the drying source is heat and wherein the top-coat composition further consists of a thermal initiator selected from the group consisting of benzoyl peroxide and coumarin peroxide from 0.05 to 3 percent by weight of the total composition.

26. The method of claim 22, wherein the film former of the top-coat composition is a methacrylate copolymer or a methacrylate terpolymer.

27. The method of claim 26, wherein the film former of the top-coat composition is selected from the group consisting of methyl methacrylate/butyl methacrylate copolymer and methyl methacrylate/butyl methacrylate/methacrylic acid terpolymer.

28. The method of claim 27, wherein the film former of the top-coat composition is selected from the group consisting of a copolymer of methyl methacrylate/butylmethacrylate and a terpolymer of methyl methacrylate/butylmethacrylate/methacrylic acid.

29. The method of claim 22, wherein the top-coat composition comprises a solvent at least 1.5 times the amount by weight of the base resin, the solvent selected from the group consisting of ethyl acetate, butyl acetate, and isopropyl alcohol.

30. The method of claim 22, wherein the base resin of the top-coat composition is a mixture of cellulose acetate butyrate 381-0.5 and cellulose acetate butyrate 381-2.0.

* * * * *

UNITED STATES PATENT AND TRADEMARK OFFICE
CERTIFICATE OF CORRECTION

PATENT NO. : 5,785,958
DATED : July 28, 1998
INVENTOR(S) : Sirdesai et al.

It is certified that error appears in the above-identified patent and that said Letters Patent is hereby corrected as shown below:

In claim 1, at line 2; in claim 8, at line 2; in claim 15, at line 2; and in claim 21, at line 5, delete "consisting of:" and insert --comprising:--.

In claim 1, at line 4; in claim 8, at line 4; in claim15, at line 4, please delete "composition;" and insert --composition; and free of nitrocellulose;--

In claim 21, at line 6, please delete "acetate butyrate from 5 to 50 percent" and insert --acetate butyrate and free of nitrocellulose from 5 to 50 percent--.

In claim 23, at line 3, and in claim 25, at line 2, please delete "consisting of a" and insert --comprises a--.

Signed and Sealed this

Fourteenth Day of September, 1999

*Attest:*

Q. TODD DICKINSON

*Attesting Officer*    *Acting Commissioner of Patents and Trademarks*